United States Patent [19]

Rivier

[11] 4,293,430

[45] Oct. 6, 1981

[54] SULFURIZED METALLIC DITHIOPHOSPHATES AND THEIR USE AS ADDITIVES FOR LUBRICATING OILS

[75] Inventor: Georges Rivier, Bron, France

[73] Assignee: Orogil, Courbevoie, France

[21] Appl. No.: 126,161

[22] Filed: Feb. 29, 1980

[30] Foreign Application Priority Data

Mar. 9, 1979 [FR] France .............................. 79/06059

[51] Int. Cl.³ .................... C10M 1/48; C10M 1/38; C10M 3/42; C10M 3/32
[52] U.S. Cl. ................................ 252/32.7 E; 72/42; 252/48.6
[58] Field of Search ..................... 252/32.7 E, 48.6; 72/42

[56] References Cited

U.S. PATENT DOCUMENTS

| | | | |
|---|---|---|---|
| 2,802,856 | 8/1957 | Norman et al. | 260/963 |
| 2,905,683 | 9/1959 | Goldsmith | 260/438.1 |
| 3,102,096 | 8/1963 | Nygaard et al. | 252/32.7 E |
| 3,288,819 | 11/1966 | Zichelaar et al. | 252/32.7 E |
| 3,899,432 | 8/1975 | Rothert et al. | 252/33 |
| 3,944,495 | 3/1976 | Wiley et al. | 252/32.7 E |
| 4,171,268 | 10/1979 | Collins | 252/32.7 E |

FOREIGN PATENT DOCUMENTS 1310171 12/1961 France .......................... 252/32.7 E

OTHER PUBLICATIONS

"Lubricant Additives", by Smalheer et al., Lezius Hills Co., 1967, p. 10.

Primary Examiner—Delbert E. Gantz
Assistant Examiner—Irving Vaughn
Attorney, Agent, or Firm—Herbert F. Schwartz; Ronald A. Schapira

[57] ABSTRACT

Metallic dithiophosphates obtained by the sulfurization of a composition containing:
 (A) from about 100 to 20 percent by weight of a metallic dithiophosphate of the formula:

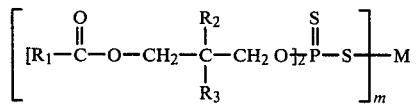

in which $R_1$ is an alkenyl or unsaturated cycloaliphatic radical, $R_2$ and $R_3$ are alkyl radicals, m is equal to the valence of the metal M, and M represents a metal of Groups IIB, IIIB, IVB, or VIII of the Periodic System of the Elements, preferably zinc;
 (B) from about zero to 80 percent of an $R_4$-$COOR_5$ alkyl ester in which $R_4$ is an alkenyl radical and $R_5$ an alkyl radical, by means of 0.5 to 10 percent by weight of sulfur, referred to the composition to be sulfurized.

Use as extreme-pressure and anti-wear additives for lubricating oils, in an amount of between about 0.3 and 15 percent of the weight of lubricating oil.

12 Claims, No Drawings

SULFURIZED METALLIC DITHIOPHOSPHATES AND THEIR USE AS ADDITIVES FOR LUBRICATING OILS

BACKGROUND OF THE INVENTION

The present invention relates to new sulfurized or co-sulfurized metallic dithiophosphates and their use as extreme-pressure and anti-wear additives for lubricating oils.

U.S. Pat. No. 3,944,495 discloses that automatic transmission fluids can be improved by the addition of metallic dithiophosphates of the formula:

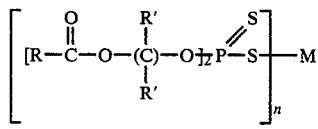

in which:

R represents a $C_4$–$C_{30}$ saturated aliphatic radical;

R' represents hydrogen, a $C_1$–$C_6$ alkyl radical or a $C_6$–$C_9$ aryl radical;

a is a whole number between 2 and 12;

n corresponds to the valence of the metal M; and

M represents an alkaline or alkaline-earth metal or a transition metal.

Such products are particularly well adapted for the problem associated with automatic transmission fluids, which do not require additives of great thermal stability. On the other hand, such products are not sufficiently thermally stable to be used as additives for crankcase oils and, in particular, for diesel crankcase oils.

It is also known that the properties of lubricating oils can be improved, according to French patent No. 1,310,171 (U.S. counterpart, U.S. Pat. No. 3,102,096), by using metallic dialkyl dithiophosphates prepared from monoalcohols of the "neo" type, that is to say, alcohols in which the carbon atom adjacent the carbon atom fixed to the hydroxyl group is completely replaced by alkyl groups. Such products have the drawback of being only of average effectiveness and, furthermore, of not being capable of industrial use because of the high cost of the "neo" monoalcohols.

By the present invention new thermally stable sulfurized or co-sulfurized metallic dithiophosphates have been discovered which can be used industrially, in particular, to improve the extreme-pressure and anti-wear properties of lubricating oils.

It is an object of the present invention to provide novel sulfurized metallic dithiophosphate oil additives which improve the extreme-pressure and anti-wear properties of lubricating oils which overcome the disadvantages of the prior art.

It is another object of the present invention to provide a novel process for the preparation of the sulfurized metallic dithiophosphate lubricating oil additives of the invention.

It is a further object of the invention to provide novel lubricating oil compositions containing the sulfurized metallic dithiosphophate additives of the invention.

Other objects will be apparent to those skilled in the art from the present description.

GENERAL DESCRIPTION OF THE INVENTION

The sulfurized metallic dithiophosphates of the present invention are obtained by sulfurization of a composition containing:

(A) from about 100 to 20 percent, and preferably about 100 to 50 percent, of a metallic dithiophosphate of formula (I):

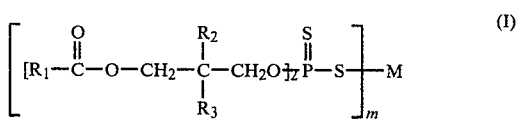

in which formula:

$R_1$ represents:
  (a) a linear or branched alkenyl radical containing from about 2 to 24 carbon atoms, and preferably from about 7 to 17 carbon atoms, optionally substituted by at least one phenyl group,
  (b) an unsaturated cycloaliphatic or polycycloaliphatic radical containing from about 3 to 20 carbon atoms, optionally substituted by one or more alkyl groups containing from about 1 to 12 carbon atoms;

$R_2$ and $R_3$ are similar or different and represent an alkyl radical containing from about 1 to 12 carbon atoms and, preferably, from about 1 to 4 carbon atoms;

m represents the valence of the metal M;

M represents a metal of group IIB, IIIB, IVB, or VIII of the Periodic System of the Elements, particularly zinc, and (B) from about zero to 80 percent, and preferably about zero to 50 percent, of an alkyl ester of formula II:

in which formula:

(a) $R_4$ represents a linear or branched alkenyl radical containing from 2 to 24 carbon atoms, and preferably from 7 to 17 carbon atoms, and (b) $R_5$ represents an alkyl radical containing from 1 to 12 carbon atoms, and preferably from 1 to 4 carbon atoms, employing a sulfurization agent in an amount corresponding to a weight of sulfur of between about 0.5 and 10 percent referred to the weight of composition to be sulfurized, and preferably between about 1 and 5 percent.

The said sulfurization operation can be carried out in accordance with conventional sulfurization techniques by means of sulfur or sulfur chlorides. For example, it can be effected by means of sulfur at a temperature above about 150° C., and generally between about 170° and 220° C. It can also be carried out with the use of $S_2Cl_2$ at a temperature of between about 60° and 100° C., followed by a dehydrochlorination operation at a temperature of between about 120° to 180° C. It is preferable, particularly for economic considerations, to carry out this operation with the use of sulfur.

Among the metallic diothiophosphates which can be used to prepare the products forming the object of the invention, particular mention may be made of those compounds of formula (I), above, in which $R_1$ represents a heptadecenyl, decenyl or $C_{19}H_{29}$ radical derived from abietic acid. $R_2$ and $R_3$ preferably represent a methyl, ethyl, or butyl radical.

Among the alkyl esters which can be used to prepare the products of the invention, particular mention may be made of those esters of formula (II), above, in which:

$R_4$ represents a heptadecenyl or decenyl radical;

$R_5$ represents a methyl, ethyl, or butyl radical.

The metallic dithiophosphates of formula (I) which may be employed can be prepared by the action of a basic compound of the metal M, and in particular by the action of zinc oxide, on a dithiophosphate acid of formula (III), below:

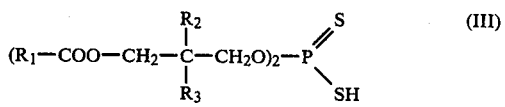

in which $R_1$, $R_2$, and $R_3$ have the meaning given above, with an amount of basic compound of metal M which is between the amount stoichiometrically necessary to neutralize the said dithiophosphoric acid and twice said stoichiometric amount.

This operation can be carried out at a temperature of between about 20° and 200° C., and preferably between about 60° and 150° C., with an amount of basic compound of metal M of preferably between about 1.1 times and 1.5 times the stoichiometric amount.

The dithiophosphoric acid of formula (I) can be prepared by the action of phosphorus pentasulfide on a mono ester alcohol of formula IV, below:

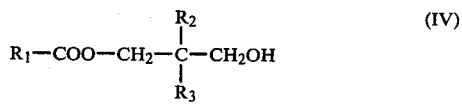

in which $R_1$, $R_2$, and $R_3$ have the meaning given above, with an amount of $P_2S_5$ representing an excess of about 5 to 20 mol percent, referred to the amount of $P_2S_5$ stoichiometrically necessary.

This operation can be carried out at a temperature of between about 50° and 200° C., and preferably between about 70° and 150° C., with an amount of $P_2S_5$ corresponding preferably to an excess of about 5 mol percent referred to the stoichiometric amount.

The monoesteralcohol of formula (IV) can be prepared by action of an acid of formula $R_1COOH$, in which $R_1$ has the meaning given above, with a diol of formula (V), below:

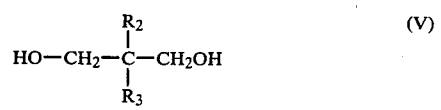

in which $R_2$ and $R_3$ have the meaning given above, with a molar ratio of acid to diol of between about 1:1 and 1:15 and preferably between about 1:2 and 1:12. This operation can be carried out at a temperature of between about 50° and 300° C., and preferably between about 80° and 200° C., in the presence of an acid catalyst.

Among the acids of formula $R_1COOH$ which can be used are oleic acid, undecylenic acid, and abietic acid.

Among the diols of formula (V) which can be employed are neopentylglycol, 2-ethyl-2-n-butyl-1,3-propanediol.

Another particularly important object of the present invention is the use of the above-described sulfurized or co-sulfurized metallic dithiophosphates as extreme-pressure and anti-wear additives for lubricating oils.

Among the lubricating oils which can be improved by addition of the said sulfurized or co-sulfurized dithiophosphates are the natural oils of a viscosity of between 20.6 cst (centistokes) and 541 cst at 37.8° C., (namely, between 100 and 2500 SUS (Saybolt Universal Viscosity) at 100° F.), or the synthetic or semi-synthetic bases (synthetic hydrocarbons, esters, polyesters, polyethers, etc.) of comparable viscosity.

The amounts of the said sulfurized or co-sulfurized dithiophosphates which are desirably introduced into the lubricating oils are between about 0.3 and 15 percent by weight of the lubricating oil. The preferred amounts of sulfurized dithiophosphates employed are a function of the future use of the oil, namely, crankcase oil, automatic transmission oil, hydraulic fluid, or cutting oil for the machine industry.

Anti-oxidant, anti-corrosion, anti-foam, detergentdispersant additives, and other extreme-pressure and anti-foam additives, etc., can be introduced without encountering any problem with respect to compatibility or loss of level of performance.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Sulfurization of zinc-bis-0,0-(2,2-dimethyl-1,3-propanediylmonooleate)-dithiophosphate of the formula

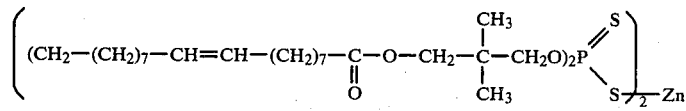

(a) Preparation of the monooleate of 2,2-dimethyl-1,3-propanediol

Into a one-liter, three-neck round-bottom flask there were introduced:

282 g. (namely, 1 mol) of oleic acid;

416 g. (namely, 4 mols) of neopentylglycol (about 1 percent water); and 14 g. of acid earth having a base of hydrochloric acid (CLARCIL earth, marketed by Sud-Chemie AG).

Heating of the mixture is effected at 180° C., for 4 hours, maintaining a pressure of 50 mm. Hg; 24.5 g. of water distill off.

After cooling the remaining mixture, 300 g. of hexane and 100 g. of water were added. The mixture was agitated for 30 minutes, whereupon the organic layer was separated by settling. This washing operation was repeated three times. The organic phase collected was distilled in order to eliminate the solvent. In this way, there were recovered 356 g. (namely, 0.967 mol) of the desired ester, having a purity of 95.6 percent (determined by nuclear magnetic resonance), the remaining impurity being neopentyl glycol. The yield of ester was 96.7 percent referred to the oleic acid.

(b) Preparation of bis-0,0-(2,2-dimethyl-1,3-propanediyl monooleate)-dithiophosphoric acid Into a one-liter, three-neck round-bottom flask there were introduced 346.4 g. (namely, 0.9 mol) of the above prepared ester, and then, over the course of 3 hours, 50 g. (namely, 0.225 mol) of phosphorus pentasulfide, maintaining the temperature at 115° C. After the addition of $P_2S_5$, the temperature was maintained at 115° C. for 30 minutes, whereupon the traces of $H_2S$ resulting are eliminated by gradually decreasing the pressure to 30 mm. of mercury. There are obtained 380 g. of the desired dithiophosphoric acid, the composition of which, determined by elementary analysis, was:

|  | Calculated | Found |
|---|---|---|
| Phosphorus | 3.73% | 3.6% |
| Sulfur | 7.71% | 7.2% |

(c) Neutralization by zinc oxide

Into a one-liter, three-neck round bottom flask there were introduced 380 g. (namely, 0.46 mol) of the above-prepared dithiophosphoric acid and thereupon, within the course of 1 hour, 22.3 g. (namely, 0.276 mol) of zinc oxide (which represents a 30 percent excess over the stoichiometric quantity), maintaining the temperature at 105° C. After the addition of the zinc oxide, the pressure was gradually decreased to 30 mm. of mercury in order to eliminate the water of formation. After cooling, the medium was taken up in 500 ml. of hexane and then filtered to remove the excess zinc oxide.

In this way there are obtained 315 g. of zinc-bis-0,0-(2,2-dimethyl-1,3-propanediyl-monooleate)-dithiophosphate, which is a viscous, clear, slightly colored compound having a pH of 5.2.

The composition of the product obtained, determined by elementary analysis, is as follows:

|  | Calculated | Found |
|---|---|---|
| Phosphorus | 3.60% | 3.7% |
| Zinc | 3.78% | 3.5% |
| Sulfur | 7.43% | 7.2 |

(d) Sulfurization 100 g. of the above-prepared zinc dithiophosphate were introduced into a three-neck flask. Heating was effected at about 218° to 220° C., whereupon 4 g. of flowers of sulfur were added (namely, 4 percent by weight), maintaining the the temperature at 218°-220° C. for 2 hours.

A colored oil was obtained having the following composition:

|  | Found |
|---|---|
| Phosphorus | 3.3% |
| Zinc | 2.96% |
| Sulfur | 8.3% |

EXAMPLE 2

100 g. of the zinc dithiophosphate obtained in Example 1, part (c), were sulfurized by the method of operation described under Example 1, part (d), using 2 g. of flowers of sulfur instead of 4 g.

The product obtained had the following composition:

|  | Found |
|---|---|
| Phosphorus | 3.28% |
| Zinc | 4.26% |
| Sulfur | 7.18% |

EXAMPLE 3

Co-sulfurization of zinc-bis-0,0-(2,2-dimethyl-1,3-propanediyl monooleate)-dithiophosphate and ethyl oleate 100 g. of the zinc dithiophosphate obtained in Example 1, part (c), and 50 g. of ethyl oleate were charged. Heating was effected at 210°-215° C. 6 g. of flowers of sulfur were added (namely, 4 percent by weight) and the temperature was maintained at 210°-215° C. for 2 hours.

152 g. of a product having the following composition were obtained:

|  | Found |
|---|---|
| Phosphorus | 2% |
| Zinc | 1.9% |
| Sulfur | 7.2% |

EXAMPLE 4

Sulfurization of zinc-bis-0,0-(2,2-dimethyl-1,3-propanediyl monoundecenoate)-dithiophosphate of the formula:

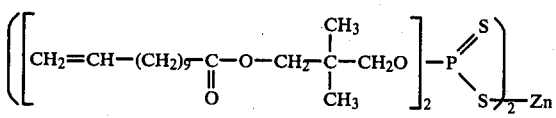

(a) Preparation of 2,2-dimethyl-propanediol undecenoate

The operation described in Example 1, part (a), was repeated, starting with:

184 g. (namely, 1 mol) of undecenoic acid;
416 g. (namely, 4 mols) of neopentylglycol; and
14 g. of CLARCIL for 5 hours at 150° C.

248 g. of the desired ester were recovered in a yield of 90 percent and a purity of 98 percent.

(b) Preparation of bis-0,0-(2,2-dimethyl-1,3-propanediylmonoundecenoate)-dithiophosphoric acid The operation described in Example 1, part (b), was repeated, starting with:

165 g. (namely, 0.6 mol) of the above-prepared ester (part (a) of this example); and 33.5 g. (namely, 0.15 mol) of P₂S₅.

There were obtained 180 g. of the desired dithiophosphoric acid having the following composition:

|            | Calculated | Found |
|------------|------------|-------|
| Phosphorus | 4.89%      | 4.7%  |
| Sulfur     | 10.09%     | 9.9%  |

(c) Neutralization by zinc oxide

The operation described in Example 1, part (c), was repeated, starting from:

127 g. (namely, 0.2 mol) of the above-prepared dithiophosphoric acid; and 10.5 g. (namely, 0.13 mol) of ZnO (30 percent excess).

There were thus obtained 115 g. of zinc-bis-0,0-(2,2-dimethyl-1,3-propanediyl monoundecenoate)-dithiophosphate of a pH of 5.1, the composition of which was as follows:

|            | Calculated | Found |
|------------|------------|-------|
| Phosphorus | 4.66%      | 4.5%  |
| Zinc       | 4.88%      | 4.7%  |
| Sulfur     | 9.62%      | 9.5%  |

(d) Sulfurization 100 g. of the above-prepared zinc dithiophosphate were introduced. Heating was effected at about 215°-218° C., 4 g. of flowers of sulfur were added, and the temperature was maintained at 215°-218° C. for 2 hours.

101 g. of a product were obtained which had the following composition:

|            | Found |
|------------|-------|
| Phosphorus | 4.4%  |
| Zinc       | 4.5%  |
| Sulfur     | 10.9% |

EXAMPLE 5

Co-sulfurization of zinc-bis-0,0-(2,2-dimethyl-1,3-propanediyl undecenoate)-dithiophosphate and methyl undecenoate The operation described in Example 3 was repeated starting with 100 g. of the zinc dithiophosphate obtained in Example 4, part (c), 50 g. of methyl undecenoate, and 6 g. of flowers of sulfur.

There were obtained 154 g. of a product having the composition:

|            | Found |
|------------|-------|
| Phosphorus | 2.5%  |
| Zinc       | 2.6%  |
| Zulfur     | 9.5%  |

EXAMPLE 6

Sulfurization of zinc-bis-0,0-(2,2-dimethyl-1,3-propanediyl-monoabietate)-dithiophosphate of the formula

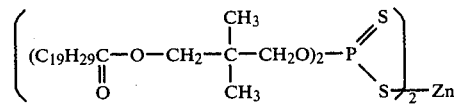

(a) Preparation of 2,2-dimethyl-1-propanol monoabietate

The operation described in Example 1, part (a), was repeated, starting with:

293 g. (namely, 1 mol) of abietic acid;

146 g. (namely, 4 mols) of neopentylglycol; and 14 g. of CLARCIL for 5 hours at 150° C.

280 g. of the desired ester were recovered in a yield of 70 percent and a purity of 95 percent.

(b) Preparation of bis-0,0-(2,2-dimethyl-1,3-propanediyl monoabietate)-dithiophosphoric acid The operation described in Example 1, part (b), was repeated, starting with:

240 g. (namely, 0.6 mol) of the above-prepared ester; and 33.5 g. (namely, 0.15 mol) of P₂S₅.

There were obtained 250 g. of the desired dithiophosphoric acid having the following composition:

|            | Calculated | Found |
|------------|------------|-------|
| Phosphorus | 3.64%      | 3.5%  |
| Sulfur     | 7.51%      | 7.5%  |

(c) Neutralization by zinc oxide

The operation described in Example 1, part (c), was repeated, starting with:

170 g. (namely, 0.2 mol) of the above-prepared dithiophosphoric acid;

10.5 g. (namely, 0.13 mol) of ZnO (30 percent excess)

In this way there were obtained 165 g. of zinc-bis-0,0-(2,2-dimethyl-1,3-propanediyl-monoabietate)-dithiophosphate of a pH of 5.2, the composition of which was as follows:

|            | Calculated | Found |
|------------|------------|-------|
| Phosphorus | 3.51%      | 3.4%  |
| Zinc       | 3.68%      | 3.4%  |
| Sulfur     | 7.24%      | 7.0%  |

(d) Sulfurization

The operation described in Example 1, part (d), was repeated, starting with:

100 g. of the above-prepared zinc dithiophosphate; and 2 g. of flowers of sulfur at a temperature of 218° C. for 3 hours.

An oil having the following composition was obtained:

|            | Found |
|------------|-------|
| Phosphorus | 3.2%  |
| Zinc       | 3.0%  |

|  | Found |
|---|---|
| Zulfur | 8.6% |

EXAMPLE 7

Co-sulfurization of zinc-bis-O,O-(2,2-dimethyl-1,3-propanediyl-monoabietate)-dithiophosphate and methyl oleate The operation described in Example 3 was repeated, starting with:

100 g. of the zinc dithiophosphate obtained in Example 6, part (c);
100 g. of methyl oleate; and
4 g. of flowers of sulfur (namely, 2 percent by weight) at a temperature of 218° C. for 3 hours.

The product obtained had the following composition:

|  | Found |
|---|---|
| Phosphorus | 1.6% |
| Zinc | 1.5% |
| Sulfur | 5.2% |

EXAMPLE 8

Co-sulfurization of zinc-bis-O,O-(2,2-dimethyl-1,3-propanediylmonoundecenoate)-dithiophosphate and butyl oleate The operation described in Example 3 was repeated, starting with:

100 g. of the zinc dithiophosphate obtained in Example 4, part (c);
25 g. of butyl oleate; and
3.4 g. of sulfur (namely, 3 percent by weight) at 215° C. for 3 hours.

128 g. of product of the following composition were obtained:

|  | Found |
|---|---|
| Phosphorus | 3.9% |
| Zinc | 4.0% |
| Sulfur | 12.5% |

EXAMPLE 9

Sulfurization of zinc-bis-O,O-(2-ethyl-2-n-butyl-1,3-propane diyl-monooleate)-dithiophosphate of the formula:

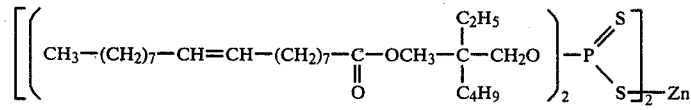

(a) Preparation of 2-ethyl-2-n-butyl-1-propanol monooleate

The operation described in Example 1, part (a), was repeated, starting with:

282 g. (namely, 1 mol) of oleic acid;
640 g. (namely, 4 mols) of 2-ethyl-2-n-butyl-1,3-propane diol; and
14 g. of CLARCIL for 4 hours at 170° C.

402 g. of the desired ester were recovered with a yield of 91 percent and a purity of 96 percent.

(b) Preparation of bis-O,O-(2-ethyl-2-n-butyl-1,3-propanediylmonooleate)-dithiophosphoric acid The operation described in Example 1, part (b), was repeated, starting with:

265 g. (namely, 0.6 mol) of the above-prepared ester; and
33.5 g. of the (namely, 0.15 mol) of P$_2$S$_5$.

280 g. of the desired dithiophosphoric acid were obtained having the following composition:

|  | Calculated | Found |
|---|---|---|
| Phosphorus | 3.29% | 3.40% |
| Sulfur | 6.79% | 6.80% |

(c) Neutralization by zinc oxide

The operation described in Example 1, part (c), was repeated, starting with:

188.5 g. (namely, 0.2 mol) of the above-prepared dithiophosphoric acid;
10.5 g. (namely, 0.13 mol) of ZnO (30 percent excess).

180 g. of zinc-bis-O,O-(2-ethyl-2-n-butyl-1,3-propanediyl-monooleate)-dithiophosphate were obtained having a pH of 5.8 and the composition of which was as follows:

|  | Calculated | Found |
|---|---|---|
| Phosphorus | 3.18% | 3.2% |
| Zinc | 3.34% | 3.2% |
| Sulfur | 6.57% | 6.6% |

(d) Sulfurization

The operation described in Example 1, part (d), was repeated, starting with:

100 g. of the above-prepared zinc dithiophosphate; and
3 g. of flowers of sulfur at 215° C. for 3 hours.

102 g. were obtained of a product having the following composition:

|  | Found |
|---|---|
| Phosphorus | 3.2% |
| Zinc | 3.1% |
| Sulfur | 9.4% |

EXAMPLE 10

A series of lubricating compositions were prepared by adding to a 10 W 30 oil in each case an amount of the additive product obtained in each of Examples 1 to 9, inclusive, corresponding to 0.1 percent phosphorus.

The mechanical properties of this composition were tested on:

1. A 4-ball machine in accordance with ASTM Standard D 2783-69 T; this test gives the diameter in millimeters of the imprint under a seizure load of 70, 90, 110, and 130 kg., as well as the welding load in kg.

2. Falex machine; this test shows the wear of the pin (that is to say, of the wear test piece) in milligrams at the end of 30 minutes under a pressure of 500 pounds (271.5 kg.).

The resistance to oxidation of these compositions was evaluated by the Mobil oxidation test consisting of oxidizing 33 g. of oil containing the additive, heating it at 180° C. for 50 hours in the presence of oxidation catalysts (Pb-Cu), under a flow of air of 14 liters per hour, and measuring the increase in viscosity at 210° F. (98.9° C.) of the oxidized oil as compared with new oil.

Comparable tests were carried out on compositions in which the additive product of Examples 1 to 9, was replaced by the same amount, expressed in percent of phosphorus, of one of the following commercial additives all containing phosphorus:

Additive A: "Eca 5215" marketed by Exxon
Additive b: "Lubrizol 797" marketed by Lubrizol
Additive C: "Improvex 33" marketed by Rhone-Poulenc
Additive D: "Oloa 260" marketed by Oronite
Additive E: "Oloa 269" marketed by Oronite The results of all of these tests is set forth in Table I, below.

constancy of these performances despite oxidation. The anti-oxidant properties are also very good.

EXAMPLE 11

Lubricating compositions were prepared by adding to a 10 W 30 oil the products prepared in Examples 1, 2, and 3 in different concentrations. These compositions were tested in accordance with the methods described in the proceding example; these compositions were furthermore tested on the 4-ball machine under a load of 150 kg. The results of these tests are set forth in Tables II and III, below.

TABLE II

| Product of Examples | % by Weight of Product | Mechanical Properties | | | | | | After Oxidation Seizure | Oxidation Increase |
|---|---|---|---|---|---|---|---|---|---|
| | | Before Oxidation | | | | | | | |
| | | Seizure Imprint in mm. | | | | Welding Load in kg. | Falex in kg. | Imprint in mm. 100 kg. | in Viscosity in % |
| | | 70 kg. | 90 kg. | 110 kg. | 130 kg. | | | | |
| 1 | 0.1 | 2.6 | 2.8 | — | — | 200 | broken | — | 600 |
|   | 1.5 | 2   | 2.2 | — | — | 300 | 48.5 | 1.8 | 90 |
|   | 3.0 | 0.4 | 1.8 | — | — | 300 | 6.7 | 1.7 | 70 |
|   | 4.5 | 0.4 | 1.5 | 2.5 | — | 300 | 11.1 | 1.8 | 25 |
| 2 | 0.1 | 2.6 | — | — | — | 250 | broken | — | gel |
|   | 1.5 | 1.5 | 2.2 | — | — | 250 | 14.2 | — | gel |
|   | 3   | 0.4 | 1.5 | — | — | 300 | 8.2 | 1.9 | 80 |
|   | 4.5 | 0.4 | 0.4 | 2.3 | — | 300 | 10.5 | 1.8 | 60 |
| 3 | 0.1 | 2.6 | 2.8 | — | — | <200 | broken | — | 600 |
|   | 1.5 | 2   | 2.2 | — | — | 300 | 38.0 | 1.9 | 90 |
|   | 3.0 | 1.5 | 2.1 | — | — | 300 | 1.5 | 1.8 | 70 |
|   | 5   | 0.8 | 1.5 | 2.8 | — | 300 | 0.7 | 1.7 | 30 |

It is noted that these compositions have a very good general level of performance with respect to their mechanical and anti-oxidant properties.

EXAMPLE 12

A lubricating composition was prepared by adding to a 10 W 30 oil an amount of product obtained in Examples 1 and 3 corresponding to 0.1 percent phosphorus.

Lubricating compositions were also prepared by addition of 0.1 percent phosphorus of additives D, B, and E.

These compositions were tested as to their thermal

TABLE I

| Product of Examples | % by Weight of Product | Mechanical Properties | | | | | | After Oxidation Seizure | Oxidation Increase |
|---|---|---|---|---|---|---|---|---|---|
| | | Before Oxidation | | | | | | | |
| | | Seizure Imprint in mm. | | | | Welding Load in kg. | Falex in kg. | Imprint in mm. 100 kg. | in Viscosity in % |
| | | 70 kg. | 90 kg. | 110 kg. | 130 kg. | | | | |
| 1 | 3 | 0.4 | 1.8 | — | | 300 | 6.7 | 1.7 | 70 |
| 2 | 3 | 0.4 | 1.5 | — | | 300 | 8.2 | 1.9 | 80 |
| 3 | 5 | 0.8 | 1.5 | 2.8 | | 300 | 0.7 | 1.7 | 30 |
| 4 | 2.3 | 0.45 | 2.0 | — | | 300 | 7.0 | 1.6 | 80 |
| 5 | 4 | 0.4 | 1.9 | 2.4 | | 300 | 4.7 | 1.8 | 70 |
| 6 | 3.1 | 0.5 | 2.0 | — | | 300 | 3.9 | 1.7 | 60 |
| 7 | 6.25 | 0.4 | 1.9 | — | | 300 | 5.1 | 1.8 | 70 |
| 8 | 2.6 | 0.5 | 1.9 | — | | 300 | 5.2 | 1.8 | 60 |
| 9 | 3.1 | 0.3 | 1.6 | — | | 300 | 7.5 | 1.7 | 70 |
| A | 3.73 | — | 0.5 | 0.5 | 2.5 | 300 | 8.7 | 2.0 | 80 |
| B | 4.08 | — | 2.6 | — | — | 200 | 1.0 | — | gel |
| C | 1.24 | — | 2.5 | — | — | 250 | 14.9 | — | gel |
| D | 3.45 | — | 2.6 | — | — | 300 | 23.0 | 2.4 | 90 |
| E | 1.35 | — | 0.5 | 2.2 | — | 250 | 10.5 | 2.6 | 150 |

It is noted that the additive compositions of the invention have a good general level of performance with respect to their mechanical properties and show a good stability by the Cincinnati/Milacron Test; this test consists in holding the compositions at 135° C. for 138 hours in the presence of iron and copper and then measuring the following parameters:

(a) change in the weight of the iron and copper test pieces;
(b) weight of sediment;
(c) coloring of the copper test piece (ASTM Test D 130);
(d) increase in viscosity.

The results of this test appear in Table III, below.

TABLE III

| Product | Fe Test Piece | Cu Test Piece | Weight of Sediment mg. | Increase in Viscosity in % | Appearance | Copper Strip ASTM D 10 |
|---|---|---|---|---|---|---|
| Ex. 1 | −0.2 mg. | − 4.9 mg. | 0 | 7 | clear | 2 C |
| Ex. 3 | +0.8 mg. | −13.1 mg. | 1 | 10 | clear | 2 C |
| D | +0.8 mg. | −23.7 mg. | 21 | 50 | cloudy | 4 a |
| B | −1 mg. | −66.7 mg. | 10 | 30 | cloudy | 4 a |
| E | +0.4 mg. | −20.3 mg. | 31 | 15 | clear | 4 b |

It can be noted that the compositions obtained with the products of Examples 1 and 3 show very good thermal stability as compared with the commercial products, without corrosion of the iron or copper.

EXAMPLE 13

Composition I

There was prepared a lubricating composition (I) having a base of a base oil mixture corresponding to a 15 W 40 oil containing 5 percent of a package of additives formed of:

(A) 35 percent of a dispersant having a base of an alkenyl succinimide obtained by reacting a succinic anhydride substituted by a polyisobutene (number of carbon atoms between 50 and 60) with triethylene tetramine;

(B) 15 percent of a detergent having a base of a neutral calcium salt of a sulfonic acid;

(C) 20 percent of a detergent having a base of calcium alkyl phenate, the alkyl radical of which contains 12 carbon atoms and the TBN of which (total base number, ASTM Standard D 2896) is greater than 200 mg. of potash per gram;

(D) 20 percent of a detergent having a base of a magnesium sulfonate of a TBN of more than 20 mg.;

(E) 1 percent of an anti-oxidant of the tertiobutylphenyl type; and (F) dilution oil.

Composition II

To the above Composition I, there was added 0.1 percent phosphorus in the form of "Oloa 269."

Composition III

To the above Composition I, there were added 0.05 percent of phosphorus in the form of "Oloa 269" and 0.05 percent of phosphorus in the form of the product obtained in Example 3.

Compositions II and III were tested by means of ASTM Test PV 1. The results of this test appear in Table IV, below.

TABLE IV

| Composition | II | III |
|---|---|---|
| A S | 9.6 | 9.7 |
| V P | 8.4 | 7.9 |
| A V | 8.5 | 7.9 |
| Wear of cams | 3.2 | 0.7 |

TABLE IV-continued

| Composition | II | III |
|---|---|---|
| Maximum wear | 7.2 | 0.9 |

AS = Average sludge = Average value of the sludge
VP = Varnish piston = Varnish on the pistons
AV = Average varnish = Average value of the varnish It can be noted that Composition III had very good characteristics with respect to the wear of cams, while having good properties with respect to sludge and varnish.

EXAMPLE 14

The purpose of this example was to show the improvement made by the additive products of the invention with regard to the losses in energy by friction in internal combustion engines. The test consisted in examining the resistant torque produced by the driving of said engine by an electric motor rotating at 1500, 3000, and 5500 rpm, the temperature of the oil being maintained at 100° C.

It was noted that the energy absorbed when Composition III is used was less than 10 percent of the absorbed when the Composition II was used.

As will be apparent to those skilled in the lubricant additive art from the foregoing disclosure, in each of Examples 1 through 9, inclusive, the zinc oxide employed, or the zinc dithiophosphate, can be replaced by an equivalent amount of an oxide or other basic compound, or a dithiophosphate, of a metal from Groups IIB, IIIB, IVB, and VIII of the Periodic System of the Elements. Among such metals are cadmium from Group IIB, aluminum from Group IIIB, tin and lead from Group IVB, and iron and cobalt from Group VIII. As employed throughout the present specification and the appended claims, the Periodic System of the Elements, is intended to refer that published by the Société Chimique de France. Included among the metals of group IIB are Zn, Cd and Hg; among the metals of the group IIIB are B, Al, Ga, In and Tl; among the metals of group IVB are Si, Ge, Sn and Pb; among the metals of group VIII are Fe, Co and Ni.

The terms and expressions which have been employed are used as terms of description and not of limitation, and there is not intention in the use of such terms and expressions of excluding any equivalents of the features shown and described or portions thereof, but it is recognized that various modifications are possible within the scope of the invention claimed.

What is claimed is:

1. A sulfurized metallic dithiophosphate comprising the product obtained by sulfurization of a composition containing:
   (A) from about 100 to 20 percent of a metallic dithiophosphate of formula (I):

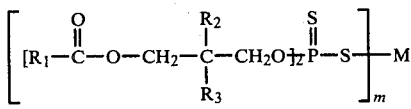

in which formula:

$R_1$ represents:
- (a) a linear or branched alkenyl radical containing from about 2 to 24 carbon atoms;
- (b) an unsaturated cycloaliphatic or polycycloaliphatic radical containing from about 3 to 20 carbon atoms;

$R_2$ and $R_3$ are similar or different and represent an alkyl radical containing from about 1 to 12 carbon atoms;

m represents the valence of the metal M;

M represents a metal of group IIB, IIIB, IVB, or VIII of the Periodic System of the Elements; and (B) from about zero to 80 percent of an alkyl ester of formula (II):

(II) $R_4$—COOR$_5$ in which:

$R_4$ represents a linear or branched alkenyl radical containing from about 2 to 24 carbon atoms, and $R_5$ represents an alkyl radical containing from about 1 to 12 carbon atoms, by means of a sulfurization agent in an amount corresponding to a weight of sulfur of between about 0.5 and 10 percent, referred to the weight of composition to be sulfurized.

2. A sulfurized metallic dithiophosphate according to claim 1, wherein the alkenyl radical of the metallic dithiophosphate is substituted by at least one phenyl group.

3. A sulfurized metallic dithiophosphate according to claim 1, wherein the cycloaliphatic or polycycloaliphatic radical is substituted by at least one alkyl group containing from about 1 to 12 carbon atoms.

4. A sulfurized metallic dithiophosphate according to claim 1, wherein a composition is sulfurized containing from about 100 to 50 percent of metallic dithiophosphate of formula (I) and about zero to 50 percent of alkyl ester of formula (II).

5. A sulfurized metallic dithiophosphate according to claim 1 wherein M is zinc.

6. A sulfurized metallic dithiophosphate according to claim 1, wherein $R_1$ contains from about 7 to 17 carbon atoms when it represents an alkenyl radical, $R_2$ and $R_3$ contain from about 1 to 4 carbon atoms, $R_4$ contains from about 7 to 17 carbon atoms, and $R_5$ contains from about 1 to 4 carbon atoms.

7. A sulfurized metallic dithiophosphate according to claim 1, wherein $R_1$ represents a decenyl or heptadecenyl radical or a $C_{19}H_{29}$ radical derived from abietic acid, $R_2$ and $R_3$ represent a methyl, ethyl, or butyl radical, $R_4$ represents a decenyl or heptadecenyl radical, and $R_5$ represents a methyl, ethyl, or butyl radical.

8. A sulfurized metallic dithiophosphate according to claim 1, wherein sulfurization is effected by means of about 1 to 5 percent by weight of sulfur, referred to the composition to be sulfurized.

9. A sulfurized metallic dithiophosphate according to claim 1, wherein the sulfurization is effected by means of sulfur at a temperature of more than 150° C.

10. A sulfurized metallic dithiophosphate according to claim 9, wherein the sulfurization is effected at a temperature of between 170° and 220° C.

11. A novel lubricating composition comprising a major proportion of at least one lubricating oil and between about 0.3 and 15 percent by weight of a sulfurized metallic dithiophosphate according to claim 1.

12. A novel lubricating composition comprising a major proportion of at least one lubricating oil and between about 0.3 and 15 percent by weight of a sulfurized metallic dithiophosphate according to claim 4.

* * * * *